United States Patent [19]

Dorsett

[11] Patent Number: 4,590,156

[45] Date of Patent: May 20, 1986

[54] AGGLUTINATION ASSAY AND PRODUCT FOR RUBELLA ANTIBODY

[75] Inventor: Preston H. Dorsett, Memphis, Tenn.

[73] Assignee: The University of Tennessee Research Corporation, Knoxville, Tenn.

[21] Appl. No.: 380,537

[22] Filed: May 21, 1982

[51] Int. Cl.[4] ................. G01N 33/546; G01N 33/547
[52] U.S. Cl. .......................... 435/5; 424/89;
435/7; 435/239; 436/532; 436/533; 436/534;
436/811
[58] Field of Search ............... 436/531, 532, 533, 534, 436/811; 424/89; 435/239, 5, 7

[56] References Cited

U.S. PATENT DOCUMENTS 4,195,074  3/1980  Safford, Jr. .
4,403,037  9/1983  Coates ............................. 435/5 X

OTHER PUBLICATIONS

Davis et al., *Microbiology*, Harper & Row, NY, 1980, 3rd Ed, p. 1198.
Vaananen and Vaheri, Applied Microbiology, Sep. 1971, vol. 22, No. 3, pp. 255–259.
Liebhaber, et al., Virology 47, 684–693 (1972).
Vaheri and Hovi, Journal of Virology, Jan. 1972, vol. 9, No. 1, pp. 10–16.
Addendum on p. 583 of the Castellano, et al. article appearing in the Journal of Infectious Diseases, vol. 143, No. 4, Apr. 1981, pp. 578–584.

*Primary Examiner*—Sidney Marantz
*Attorney, Agent, or Firm*—Elliot M. Olstein

[57] ABSTRACT

A solid support is sensitized with soluble rubella virus antigen which is obtained by disruption and solubilization of whole (intact) rubella virus. The sensitized support is useful in an assay for rubella virus antibody.

40 Claims, No Drawings

AGGLUTINATION ASSAY AND PRODUCT FOR RUBELLA ANTIBODY

This invention relates to viruses, and more particularly to the purification of virus, production of virus antigens, the use of virus antigens for the production of sensitized solids, and the use of virus antigen sensitized solids for testing for virus antibodies. Most particularly, the invention relates to rubella virus, rubella virus antigen and a test for rubella virus antibody.

U.S. Pat. No. 4,195,074 discloses a process for producing soluble rubella virus antigen, and the use thereof in an agglutination test for rubella virus antibody. In accordance with U.S. Pat. No. 4,195,074, the tissue culture from rubella virus infected cells is subjected to immunosorbent separation through a column containing IgG derived from human serum known to contain antibodies reactive with rubella antigen followed by elution of the rubella antigen material from the column and selection of the soluble antigen by gel permeation chromatography. The antigen may then be employed for sensitizing erythrocytes, and the sensitized erythrocytes are used to determine antibody in human serum samples by direct agglutination.

In accordance with the aforesaid patent, the so-called rubella antigen is not recovered from the virus, per se, and, therefore, it is believed that such material does not include structural proteins of the virus.

In accordance with one aspect of the present invention, there is provided a solid support sensitized with soluble rubella viral antigen which is obtained by disruption and solubilization of whole (intact) rubella virus.

In accordance with another aspect of the invention, soluble rubella virus antigen is obtained from whole rubella virus.

In accordance with still another aspect of the present invention, there is provided a test or assay for rubella virus antibody and a reagent kit therefor.

In accordance with a further aspect of the present invention, there is provided a process for producing purified virus by the use of an adsorption gel to remove non-viral proteins and nucleic acids.

In accordance with yet a further aspect of the invention, there is provided a method for producing a solid sensitized with a viral intigen.

More particularly, the rubella virus antigen is isolated from intact rubella virus by treating purified whole rubella virus with a surfactant or detergent which disrupts the virus to provide the soluble rubella virus antigen, without destroying the antigenic characteristics thereof. The detergent is employed in an amount that is sufficient to disrupt and solubilize the whole virus without destroying its antigenic characteristics.

The surfactant or detergent which is used for disrupting the whole rubella virus may be any one of a wide variety of surfactants or detergents which disrupt and solubilize the virus, without destroying the antigenic characteristics, including cationic, anionic and non-ionic surfactants. Such surfactants are well known in the art, and as representative examples, there may be mentioned alkali metal salts of sulfates, soaps, sulfated or sulfonated oils, various amines, quaternary salts, condensation products with ethylene oxide, etc. Such detergents and surfactants and the use thereof for disrupting whole virus are known in the art. Preferred detergents for such use are alkali (lithium or sodium) dodecyl sulfate, sulfobetain, deoxylcholate and laurolylsarcosine (Sarcosyl).

In the case where the rubella virus antigen is to be supported on a solid support for use in an agglutination assay technique, the detergent or surfactant is one which is capable of disrupting and solubilizing the virus to provide soluble virus antigen having a molecular weight such that when supported on a particle, the sensitized particle remains mono-dispersed. In general, when using the rubella virus antigen for the sensitization of a particle, the soluble antigen does not have a molecular weight in excess of 125,000, and most generally not in excess of 100,000, as determined by acrylamide gel electrophoresis.

As hereinabove indicated, the surfactant is employed in an amount which is sufficient to disrupt and solubilize the virus and which does not destroy the antigenic characteristics thereof (too much detergent may destroy the antigenic characteristics). In general, the surfactant to virus weight ratio is an amount of from 0.2:1 to about 5:1, preferably from about 0.5:1 to 1:1. The selection of an optimum amount is deemed to be within the scope of those skilled in the art from the teachings herein.

The treatment of the purified virus is effected at a temperature which does not denature the virus proteins, with such temperature generally not exceeding about 30° C., with a temperature of from 20° C. to 25° C. being most convenient. Similarly, the pH is selected so as to maintain stability, with the pH being generally at 8.5, with the optimum pH generally being in the order of from 8.0 to about 9.0.

The treatment of the purified virus with the surfactant is for a period of time sufficient to disrupt the virus and effect solubilization thereof. In general, such disruption and solubilization can be accomplished in time periods in the order of from 5 to 120 minutes, however, in some cases longer or shorter times may be applicable.

The selection of an optimum treatment time is deemed to be within the scope of those skilled in the art from the teachings herein.

Applicant has found that by using a surfactant to disrupt and solubilize the whole rubella virus, as hereinabove described, it is possible to provide soluble rubella virus antigen which retains its antigenicity.

A procedure for disruption and solubilization of whole virus, as hereinabove described, has been previously practiced in the art; for example, Vaheri et. al. "Structural Proteins and Subunits of Rubella Virus", *Journal of Virology*, P. 10–16 (January, 1972). In addition, it is known that such a procedure is capable of recovering the structural proteins of the whole rubella virus, with there being three principal structural proteins, namely a structural protein with a molecular weight in the order of from 60,000 to 65,000 daltons, a structural protein with a molecular weight in the order of from 40,000 to 50,000 daltons, and a structural protein having a molecular weight in the order of from 32,000 to 38,000 daltons. Applicant has also found evidence of a structural protein having a molecular weight of from 100,000 to 120,000 daltons.

Applicant has found that the structural proteins recovered by such a procedure retain antigenic characteristics, and in addition, such structural proteins can be used in an assay for rubella antibody. Furthermore, applicant has found that such structural proteins are capable of detecting early phase rubella antibody, i.e., the rubella antibody present in serum or plasma within ten days of onset of rubella rash. The term "rubella virus antigen" as used herein encompasses one or more of such structural proteins recovered by such procedure.

The hereinabove described technique for disruption and solubilization of whole rubella virus to provide soluble rubella virus antigen is also applicable to providing virus antigen from other viruses; e.g., those hereinafter disclosed with reference to a purification of virus. Such viral antigens may then be supported on a solid support, as hereinafter described, to provide a solid sensitized with the viral antigen for use in an assay.

In accordance with an aspect of the present invention, applicant has found that disruption and solubilization of whole rubella virus produces a soluble product which is antigenic and which is capable of reacting with rubella antibody, including the early phase antibody. Thus, by using a product prepared by such a procedure in an assay for rubella antibody; and in particular on a solid support, it is possible to detect rubella antibody even during the early phase.

As hereinafter described, the recovered product is of particular value for a direct agglutination assay, and applicant has found that such soluble rubella virus antigen may be supported on a latex particle (in particular a polystyrene) without the problem of self agglutination, i.e., the sensitized particles remain mono-dispersed.

The purified whole virus which is treated with surfacants is a virus which is produced in a tissue culture by procedures known in the art, and which is subsequently purified to remove non-virus lipids, nucleic acids, and non-viral proteins.

The tissue culture growth of rubella virus wherein rubella virus infected cells are raised in a suitable culture medium is well known in the art. The cells that are suitable for tissue culture growth to produce the rubella virus includes Vero cells, Baby Hamster Kidney, Procine Stabile Kidney, Serum Institute Rabbit Cornea and the like. In general, tissue cultures conventionally used for producing rubella virus are also suitable for the purposes of the present invention.

The virus may then be purified by procedures known in the art; e.g. as disclosed by Baheri et. al., supra. In accordance with a preferred embodiment, the virus is purified in accordance with a procedure of the present invention.

More particularly, the procedure for purifying virus in accordance with the invention, involves, treating concentrated virus with hydroxyl apatite gel in an aqueous solution of controlled ionic strength and pH.

More particularly, after filtration and concentration, the virus is contacted with hydroxyl apatite gel in an aqueous solution having an ionic strength which is great enough to minimize or prevent adsorption of the virus by the gel, and which is low enough to allow the non-virus proteins to be adsorbed by the gel. The ionic strength is maintained by the use of phosphate ions, with the phosphate ions being present at a molarity of from 0.05M to 1.5M to provide for effective adsorption of non-virus proteins and nucleic acids, without significant adsorption of the virus. The phosphate molarity in most cases is at least 0.08M.

In addition, the adsoprtion is conducted at a pH in the order of from 6 to 9, most generally in the order of from 7 to 8. The pH of the solution is maintained by the use of a suitable buffer. The adsorption may be conducted in the presence of EDTA at a concentration from 0.01M to 0.0001M. EDTA as well as other chelating agents increases adsorption of non-viral proteins and nucleic acids, and aids in minimizing the adsorption of viral proteins.

By proceeding in accordance with the purification of the invention, the high molecular weight proteins and nucleic acids are adsorbed by the gel to thereby separate the virus protein from the non-viral proteins having similar molecular weights.

After such adsorption, the lower molecular weight proteins still remaining in the fluid may be separated by conventional procedures. Thus, for example, further separation may be accomplished by centrifugation through a barrier layer or cushion as known in the art. In particular, the virus protein is centrifuged through a suitable barrier layer such as sucrose, glycerol, cesium chloride, cesium sulfate and the like, with the lower molecular weight proteins remaining above the barrier, and the virus being centrifuged through the barrier, as a separate layer. The fluid containing the low molecular weight proteins and the barrier layer are then removed leaving a virus protein essentially free of non-virus proteins, nucleic acids, lipids, and the like. In general, the purified virus contains less than 1%, most generally less than 0.1% of non-virus lipids, nucleic acids and proteins.

The above procedure may be employed for purifying a wide variety of viruses, including, but not limited to: rubella virus; rubeola virus, herpeto viruses (herpes simplex, Varicella Zoster, cytomegalovirus, Epstein-Barr [infectious mono-nucleosis]); parainfluenza viruses; influenza virus; dengue virus, etc.

Such purified virus may then be treated with a surfactant to disrupt the virus and effect solubilization thereof to thereby provide a virus antigen, as hereinabove described.

It is to be understood that although the hereinabove described procedure for purifying the rubella virus is preferred, other procedures for separating non-virus proteins, lipids and nucleic acids can also be employed for purifying the rubella virus for subsequent treatment with surfactant to thereby produce the soluble rubella virus.

The viral antigen which is prepared by disruption and solubilization of whole virus may be supported on a solid support for use in an assay. The following description is particularly directed to rubella virus antigens; however, the teachings are also applicable to other viral antigens.

The rubella virus antigen prepared by disrupting and solubilizing whole rubella virus may then be supported on a solid support for use in an assay for rubella virus antibody. Such supported rubella virus antigen is capable of reacting with early phase rubella virus antibody. In accordance with the preferred embodiment, the rubella virus antigen is supported on a particulate support for use in an agglutination assay; however, it is to be understood that the rubella virus antigen may be supported on a non-particulate support (or for that matter on a particulate support) for use in an assay for rubella virus antibody by procedures other than the agglutination technique. Thus, for example, the supported rubella virus antigen may be supported on a solid support for use in an assay for rubella virus antibody by a radioimmunoassay, fluorescent or enzyme assay technique. Similarly, the rubella virus antigen of the present invention may be employed for the assay of rubella virus antibody in unsupported form by use of such techniques. Thus, the scope of the invention is not limited to the preferred embodiment wherein the rubella virus antigen is supported on a particulate support for use in an agglutination assay for rubella virus antibody.

The antigen may be supported on any one of a wide variety of solid supports which are capable of supporting the antigen, and which can be used in the assay procedure without interfering with the immunochemical reaction. Moreover, the support should be one which is stable; i.e., not adversely affected by the prepared antigen. The antigen may be supported on the support by an adsorption technique, or by covalent coupling, either by activation of the support, or by the use of a suitable coupling agent, or by use of reactive groups on the support. Such procedures are generally known in the art.

The support may be any one of a wide variety of supports, and as representative examples of suitable supports there may be mentioned: synthetic polymer supports, such as polystyrene, polypropylene, substituted polystyrene (e.g., aminated or carboxylated polystyrene), polyacrylamides, polyamides, polyvinylchloride, etc.; glass beads, agarose; etc. The supports may include reactive groups; e.g., carboxyl groups, amino groups etc. to permit direct linking of the virus antigen to the support.

In accordance with preferred embodiment, the particulate support is either a polystyrene, aminated polystyrene, carboxylated polysytrene or a polyvinylchloride, although, it is to be understood that the scope of the invention is not limited to such supports.

As hereinabove indicated, the antigen may be supported on the support by the use of an adsorption technique, or by covalent coupling with a coupling agent. As representative examples of suitable coupling agents there may be mentioned: dialdehydes; for example glutaraldehyde, succinaldehyde, malonaldehyde, etc; unsatured aldehyde, e.g., acrolein, methacrolein, crotonaldehyde, etc.; carbodiimides; diisocyanates; dimethyladipimate; cyanuric chloride etc. The selection of a suitable coupling agent should be apparent to those skilled in the art from the teachings herein.

Similarly, the antigen may be supported by activation of a suitable support; for example, cyanogen, bromide activated agarose.

In accordance with a preferred embodiment, as hereinabove noted, the soluble rubella virus antigen is supported on a particulate support which is either polystyrene (substituted or unsubstituted) or polyvinylchloride; most preferably polystyrene.

In some cases, the soluble antigen may be supported by an adsorption technique, in other cases, it may be necessary to employ covalent coupling.

The virus antigen sensitized particulate support is preferably prepared for use in an assay in which rubella virus antibody is determined by an agglutination technique. The particulate support is provided with an effective amount of the antigen for the assay, while preventing excessive amounts which may result in bridging of the antibody to a single particle. In general the weight ratio of soluble rubella antigen to support is from 1:100 to 1:5000. The selection of an optimum amount is deemed to be within the scope of those skilled in the art from the teachings herein.

In accordance with one technique, after the antigen is adsorbed on the particles, the support, including the adsorbed antigen, is further coated with protein which does not adversely affect the subsequent immunochemical reaction in order to provide a protein coating on the portion of the support which does not including the antigen. As should be apparent, the protein coating should not immunologically react with either the rubella virus antigen or with sera to be used in the assay. As examples of suitable proteins there may be mentioned: bovine serum albumin, ovalbumin, and the like. The selection of a suitable protein to saturate the spaces between the rubella virus antigen on the support is deemed to be within the scope of those skilled in the art from the teachings herein.

It is to be understood that such coating with protein is not required for producing sensitized particles for use in an agglutination assay.

After the rubella virus antigen has been supported on a solid support, as generally practiced in the art for the production of sensitized particles for use in an agglutination assay, the sensitized particles are treated with a liquid containing polyoxyethylene sorbitan monolaurate (Tween 20) at a weight ratio to the polystyrene of 0.1:1 to 10:1.

The sensitized particles are preferably a synthetic polymer and in particular a polystyrene [substituted (carboxylated or aminated) or unsubstituted] or polyvinylchloride latex. Applicant has found that sensitization of such particles with soluble rubella virus antigen prepared, as hereinabove described, produces a sensitized particles which remains mono-dispersed (no self agglutination), whereby such sensitized latex particles may be effectively employed in a direct agglutination assay for rubella antibody. Such sensitized particles are capable of detecting early phase rubella antibody. In addition, such sensitized particles are capable of providing a direct agglutination assay having a high sensitivity for rubella antibody.

The rubella virus antigen sensitized particle prepared in accordance with the invention are suitable for use in a kit and assay for rubella virus antibody by a direct agglutination procedure. Such kit may include, in addition to the sensitized rubella virus particles, as hereinabove described, in a suitable container therefor, a reactive serum control (contains rubella antibody) and a non-reactive serum control (no rubella antibody) in suitable containers therefor. In accordance with a preferred embodiment, in addition to the reagents, there is provided a test card on which the assay is effected. The test card has a flat testing surface which include suitably marked areas (for example, a test circle) for placing one or more samples to be assayed, as well as suitably marked areas for each of the serum controls. The test card and reagents may be included in a single kit package.

In the agglutination assay, undiluted serum or diluted serum (e.g. 1:10) is contacted with the sensitized particles followed by mixing, with the presence of the antibody against rubella virus being evidenced by visible agglutination.

Such rubella virus antigen sensitized particles may also be employed in a quantitative assay for rubella virus antibody.

In a quantitative assay, the sample to be assayed is serially diluted, as appropriate, and to each serial dilution there is added the particles sensitized with the soluble rubella antigen. The quantity of antibody in the sample is determined from the highest dilution giving any agglutination of the sensitized particles.

The quantitative or qualitative assay for rubella antibody may be effected on a card surface wherein the surface includes suitably marked areas for placing the sample and control to which the senitized particles are added.

The invention will be further described with respect to the following examples; however, the scope of the invention is not to be limited thereby:

EXAMPLE I

Production and Purification of Rubella Virus.

Confluent roller cultures (680 cm$^2$) of Vero cells (a continuous culture line of cells derived from African Green monkey kidney) were innoculated with approximately 0.01 PFU of rubella virus per cell and maintained in a standard culture medium (Medium 199) containing 0.025M hepes buffer, pH 7.4, and 2% (vol/vol) of the filtrate obtained by forcing fetal bovine serum through a membrane designed to retain molecules of 100,000 molecular weight and greater (Amicon XM-100 membrane). The medium was changed daily, and the culture fluids having a hemagglutination titer greater than 16 were made to contain 0.01M Tris base and 0.01M EDTA. After incubation at 4° C. for 1 hour, they were concentrated in an Amicon hollow fiber dialyzer-concentrator to 1/10 the original volume. After clarification at 5,000×g for 20 minutes, the pH was adjusted to 7.6 at 22° C. and 1/10 volume of hydroxylapatite suspension was added, and the slurry was incubated at 4° C. with mixing, overnight. The hydroxylapatite was removed by centriguation at 5,000×g for 15 minutes, after which 30 ml of the concentrate was layered over 9 ml of 69% (wt/wt) glycerol in a Beckman SW28 tube. The virus was sedimented at 82,000×g for 16 hours at 4° C., and the resultant pellet was resuspended in 0.01M carbonate buffer, pH 9.5 (coating buffer). The purified virus was assayed for hemagglutinin content and stored at −70° C.

EXAMPLE II

Solubilization of Purified Virus.

The purified virus in 0.01M carbonate buffer, pH 9.5, was solubilized by treatment with sodium dodecyl sulfate (SDS). The purified virus was made to contain 0.05% (w/v) SDS and was incubated for 30 minutes at room temperature.

EXAMPLE III

Preparation of Sensitized Latex.

Commercial suspensions of polystyrene latex (0.9 micron diameter particles) were washed four times with 25 volumes each of the coating buffer and were resuspended in the coating buffer to provide 3% solids (vol/vol.). The latex suspension was added directly to the solubilized virus at a ratio of 2 volumes of the 3% latex to 1 volume of solubilized virus and the suspension was mixed by tumbling for 16 hours at room temperature. The sensitized latex was washed twice with 20 volumes of 1% bovine serum albumin in phosphate buffered saline (BSA-PBS) and resuspended at 0.5% in 1% BSA-PBS contained 0.05% polyoxyethylene sorbitan monolaurate surface active agent (Tween 20) and 0.02% gentamiacin.

EXAMPLE IV

Latex Agglutination Test for Rubella Virus Antibodies.

Glass plates with 1.4 cm fused circles were employed. Serial 2-fold dilutions of serum were prepared in 1% BSA-PBS-Tween 20 and 25 ul of each dilution was placed in separate wells. After adding 25 ul of sensitized latex, the serum and latex suspension was mixed and rotated 100 rpm for 5 minutes. The presence of antibody against rubella virus was evidenced by visible agglutination.

EXAMPLE V

Purified virus prepared in accordance with Example I was treated with a 1% aqueous solution of sarcosyl for 30 minutes at room temperature in coating buffer to disrupt and solubilize the virus.

The pH of the solubilized virus was adjusted to 6.5 with hydrochloric acid and mixed with two volumes of 3% carboxylated polystyrene latex (in phosphate buffer, pH 6.5) for 1 hour at 4° C.

To the solution was added 10 mg of a carbodiimide coupling agent and the mixture was mixed overnight at 4° C.

After centrifugation, the solids were resuspened in phosphate buffered saline (PBS) followed by centriguation and resuspension in PBS containing 1% BSA and 0.05% Tween 20.

The procedure covalently bound the soluble rubella virus antigen to the latex.

EXAMPLE VI

In accordance with a preferred procedure, there is provided a test card for rubella antibody. The test card includes a marked circle for a reactive control, a marked circle for non-reactive control, as well as one or more test sample circles.

25 ul of undiluted serum sample is placed in an appropriately marked sample circle, and 25 ul of the reactive and nonreactive controls are placed in their respective circles.

With a micropipettor, there is added sensitized latex of Example III (approximately 15 ul), followed by rotation on a rotator (about 8 minutes), and gentle hand rotation.

The card is read microscopically in the wet state under a high intensity incandescent lamp.

The reactive control should show definite agglutination and the non-reactive control should show no agglutination.

Any serum samples showing any agglutination should be reported as reactive.

Numerous modifications and variations of the present invention are possible in light of the above teachings and, therefore, within the scope of the appended claims, the invention may be practised otherwise than as particularly described.

What is claimed is:

1. A composition, comprising:
   solid particles sensitized with soluble rubella virus antigen, said sensitized particles being immunoreactive with early phase rubella antibody, said soluble rubella antigen having been obtained by disruption and solubilization of whole rubella virus.

2. The composition of claim 1 wherein the soluble rubella virus antigen has a molecular weight of no greater than 125,000 daltons as determined by acrylamide gel electrophoresis.

3. The composition of claim 1 wherein the solid particles are a polystyrene latex.

4. The composition of claim 1 wherein the solid particles are a synthetic polymer.

5. The composition of claim 4 wherein the synthetic polymer is selected from the group consisting of polyvinyl chloride, polystyrene, aminated polystyrene and carboxylated polystyrene.

6. The composition of claim 4 wherein the soluble rubella virus antigen is covalently coupled to the solid particles.

7. The composition of claim 4 wherein the soluble rubella virus antigen is adsorbed on the solid particles.

8. The composition of claim 1 wherein the soluble rubella virus antigen is obtained by disruption and solubilization of whole rubella virus with a detergent.

9. The composition of claim 8 wherein the detergent is an alkali dodecyl sulfate.

10. A process for producing solid particles sensitized with soluble rubella virus antigen, comprising:

supporting on the particles soluble rubella virus antigen which is immunoreactive with early phase rubella antibody, said soluble rubella virus antigen having been obtained by disruption and solubilization of whole rubella virus.

11. The process of claim 10 wherein the soluble rubella virus antigen has a molecular weight of no greater than 125,000 daltons, as measured by acrylamide gel electrophoresis.

12. The process of claim 10 wherein the solid particles are a polystyrene latex.

13. The process of claim 10 wherein the particles are a synthetic polymer.

14. The process of claim 13 wherein the synthetic polymer is selected from the group consisting of polyvinyl chloride, polystyrene, aminated polystyrene and carboxylated polystyrene.

15. The process of claim 13 wherein the soluble rubella virus antigen is covalently coupled to the particles.

16. The process of claim 10 wherein the soluble rubella virus antigen is obtained by disruption and solubilization of whole rubella virus with a detergent.

17. The process of claim 16 wherein the detergent is an alkali dodecyl sulfate.

18. In a kit for determining rubella virus antibody by agglutination, the improvement comprising:

said kit including in a reagent container solid particles sensitized with soluble rubella virus antigen, said sensitized particles being immunoreactive with early phase rubella antibody, said soluble rubella virus antigen having been obtained by disruption and solubilization of whole rubella virus.

19. The kit of claim 18 wherein said kit further includes a test card having a flat surface for receiving assay samples.

20. The kit of claim 19 wherein the solid particles are a polystyrene latex.

21. The kit of claim 19 and further comprising in separate reagent containers a reactive serum control of rubella antibody and a non-reactive serum control free of rubella antibody.

22. In a direct agglutination assay for rubella virus antibodies employing solid particles sensitized with soluble rubella virus antigen, the improvement comprising:

employing in the assay solid particles sensitized with soluble rubella virus antigen, said sensitized particles being immunoreactive with early phase rubella antibody, said soluble rubella virus antigen having been obtained by disruption and solubilization of whole rubella virus.

23. The assay of claim 22 wherein the soluble virus rubella antigen has been obtained by disruption and solubilization of whole rubella virus.

24. The assay of claim 22 wherein the particles are a polystyrene latex.

25. The assay of claim 22 wherein the particles are a synthetic polymer.

26. The assay of claim 25 wherein the synthetic polymer is selected from the group consisting of polyvinyl chloride, polystyrene, aminated polystyrene and carboxylated polystyrene.

27. The assay of claim 25 wherein the soluble rubella virus antigen is adsorbed on the solid particles.

28. The assay of claim 25 wherein the soluble rubella virus antigen is covalently coupled to the solid particles.

29. The assay of claim 22 wherein the soluble rubella virus antigen has been obtained by disruption and solubilization of whole rubella virus with a detergent.

30. The assay of claim 29 wherein the detergent is an alkali dodecyl sulfate.

31. In an assay for rubella virus antibody, wherein rubella virus antibody immunoreacts with rubella virus antigen, the improvement comprising:

immunoreacting in said assay rubella virus antibody with a solid support sensitized with soluble rubella virus antigen, said sensitized solid support being immunoreactive with early phase rubella antibody, said soluble rubella virus antigen having been obtained by disruption and solubilization of whole rubella virus.

32. A composition, comprising:

solid particles sensitized with soluble rubella virus antigen, said sensitized particles being immunoreactive with early phase rubella antibody.

33. The composition of claim 32 wherein the solid particles are a polystyrene latex.

34. The composition of claim 32 wherein the solid particles are a synthetic polymer.

35. The composition of claim 34 wherein the synthetic polymer is selected from the group consisting of polyvinyl chloride, polystyrene, aminated polystyrene and carboxylated polystyrene.

36. The composition of claim 32 wherein the soluble rubella virus antigen is adsorbed on the solid particles.

37. In a kit for determining rubella virus antibody by agglutination, the improvement comprising:

said kit including in a reagent container solid particles sensitized with soluble rubella virus antigen, said sensitized particles being immunoreactive with early phase rubella antibody.

38. The kit of claim 37 and further comprising in separate reagent containers a reactive serum control of rubella antibody and a non-reactive serum control free of rubella antibody.

39. The kit of claim 38 wherein the solid particles are a polystyrene latex.

40. In a direct agglutination assay for rubella virus antibodies employing solid particles sensitized with soluble rubella virus antigen, the improvement comprising:

employing in the assay solid particles sensitized with soluble rubella virus antigen, said sensitized particles being immunoreactive with early phase rubella antibodies.

* * * * *